United States Patent [19]

Fogel et al.

[11] 3,943,242
[45] Mar. 9, 1976

[54] DEODORANT COMPOSITION CONTAINING A QUATERNARY AMMONIUM SACCHARINATE SALT

[75] Inventors: Arnold W. Fogel, Montvale; Anthony F. Mercurio, Rivervale, both of N.J.

[73] Assignee: American Cyanamid Company, Stamford, Conn.

[22] Filed: Apr. 10, 1974

[21] Appl. No.: 459,526

[52] U.S. Cl. ............... 424/65; 424/DIG. 5; 424/47
[51] Int. Cl.² ........................................... A61K 7/32
[58] Field of Search ................... 424/65, 68, DIG. 5

[56] References Cited
UNITED STATES PATENTS

| | | | |
|---|---|---|---|
| 2,634,229 | 4/1953 | de Wet | 424/65 X |
| 2,857,315 | 10/1958 | Teller | 424/66 |
| 2,889,253 | 6/1959 | Berger et al. | 424/66 |
| 2,970,083 | 1/1961 | Bell | 424/68 |
| 3,553,141 | 1/1971 | Katsumi et al. | 252/106 |

*Primary Examiner*—Dale R. Ore
*Attorney, Agent, or Firm*—Charles J. Fickey

[57] ABSTRACT

An anionic, gel, cosmetic deodorant composition is provided comprising an anionic base material selected from the alkali metal salts of long chain alkanoic acids of from 16 to 22 carbon atoms, a lower alkanol and from 0.05 to 1 percent by weight, based on the weight of the total composition, of a quaternary ammonium saccharinate salt represented by the following formula:

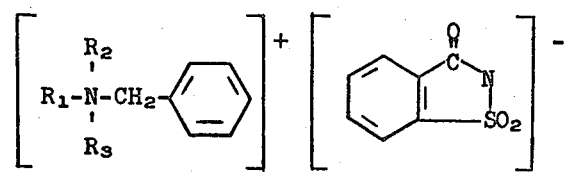

wherein $R_1$ is an alkyl radical having from 8 to 16 carbon atoms and $R_2$ and $R_3$ are either methyl or ethyl.

11 Claims, No Drawings

DEODORANT COMPOSITION CONTAINING A QUATERNARY AMMONIUM SACCHARINATE SALT

Generally stated, the subject matter of the present invention relates to an anionic, cosmetic deodorant composition. More particularly, the invention relates to a gel type anionic, cosmetic deodorant composition comprising a quaternary ammonium saccharinate.

BACKGROUND OF THE INVENTION

Various types of cosmetic compositions are known and used for the purpose of decreasing formation of perspiration, as well as preventing the formation of odoriferious products which are formed by action of surface bacteria on the perspiration.

Compositions are available as anti-perspirants for the prevention of excessive perspiration and formation of body odor. In addition, compositions are also available which contain deodorants for avoiding the formation of the odor caused by bacterial action on the perspiration.

Anti-perspirant compositions usually contain an aluminum compound as an astringent. For many people, however, the repeated use of such materials over an extended period of time is unsuitable. Compositions are also available as deodorants where the action is not based on an astringent effect, but rather on an anti-bacterial effect. However, such compositions, which depend on the anti-bacterial effect, may be unsuitable for general and extended use due to toxic side effects. In addition, there is a likelihood of development of a skin sensitivity to the anti-bacterial component. Thus, there is a need for improved deodorant compositions which on topical application have little likelihood of side effects, as well as a diminished tendency for skin sensitivity.

A convenient physical form of such a deodorant composition for topical application is the plastic stick or gel form for contact application. These compositions generally contain an anionic substance as a base, together with a lower alkanol, such as ethanol, as well as propylene glycol and a small amount of water. A preferred anionic substance is an alkali metal salt of a long chain fatty acid such as sodium stearate.

The quaternary ammonium compounds with long chain radicals which have surfactant properties are well known for their anti-bacterial activity. However, the conventional type of quaternary ammonium compound in the form of a halide, sulfate, methosulfate, and the like has been unsuitable for use in anionic, cosmetic deodorant compositions as a consequence to a loss of anti-bacterial action occasioned by an incompatability with the anionic base material.

It is, therefore, a primary object of this invention to provide a new and improved anionic, cosmetic deodorant composition.

Another object of this invention is to provide a deodorant composition which has a diminished likelihood of toxic side effects.

Still another object of this invention is to provide a new and improved deodorant composition which employs a relatively safe quaternary ammonium compound as an anti-bacterial agent.

Additional objects and advantages will be set forth in part in the description which follows, and in part will be obvious from the description, or may be learned by practice of the invention, the objects and advantages being realized and attained by means of the compositions, processes and improvements particularly pointed out in the appended claims.

THE INVENTION

To achieve the foregoing objects and in accordance with its purpose, this invention as embodied and broadly described, provides an anionic, cosmetic deodorant composition comprising an anionic base material selected from the alkali metal salts of long chain alkanoic acids of from 16 to 22 carbon atoms, a lower alkanol and from 0.05 to 1 percent of a quaternary ammonium saccharinate salt represented by the following formula:

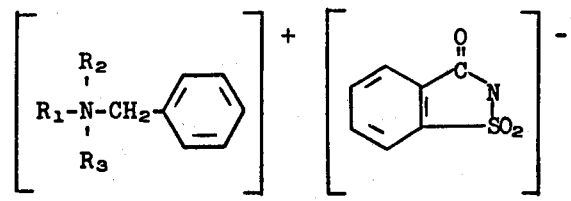

wherein $R_1$ is an alkyl radical having from 8 to 16 carbon atoms, $R_2$ and $R_3$ are either methyl or ethyl.

It is to be understood that both the foregoing general description and the following detailed description are exemplary and explanatory, but are not restrictive of the invention.

The present invention resides in the discovery that quaternary ammonium saccharinate salts when used in gel type, anionic, cosmetic deodorant compositions retain their anti-bacterial properties and result in highly effective and desirable deodorant compositions for topical applications. Such compositions are substantially non-irritating, non-stinging and non-staining to clothes and are effective over an extended period as deodorant compositions for personal use.

In the compositions of the present invention, the base materials are conventional, that is, the alkaline metal salts of long chain carboxylic acids of from 16 to 22 carbon atoms are employed. A preferred salt is sodium stearate. The gel is formed by the combination of the salt with a lower alkanol, preferably ethanol because of its overall desirable properties for such an application. In addition, a compound such as glycerine or a glycol like propylene glycol may replace all or part of the alcohol. Also, other conventional cosmetic emollients or solubilizers may be included in small amounts.

Although various quaternary compounds with cations corresponding to the cations of the saccharinates mentioned above have been available, use of such quaternary compounds in the forms of the chlorides or sulfates has not been practical in the presence of an anionic compound, such as sodium stearate. The incompatability of the compounds results in a substantial inactivation of anti-bacterial activity. A composition which is illustrative of the invention consists of ethanol, sodium stearate and the quaternary ammonium saccharinate. The quaternary ammonium saccharinate is present at a concentration of from about 0.05 to 1 percent, while the sodium stearate is present at a concentration of from about 5 to 10 percent based on the total weight of the composition.

A preferred composition consists of 0.25 percent of the quaternary ammonium saccharinate and 7.5 percent of sodium stearate. The remainder of the composition consists of alcohol to form the gel, together with conventional additives such as a perfume, a colorant and the like. With a composition tailored to be suitable for a deodorant mode of application, the new composition could also be applied by other conventional means through the use of an excess of solvent, or for example by inclusion of a solvent and a propellent for an aerosol pressure can type of application. The gel stick form of the composition affords an effective underarm deodorant without the use of a phenolic type anit-bacterial which are often found to be objectionable for a variety of reasons.

The quaternary ammonium saccharinates suitable in the composition are those defined above. Preferred compounds are those where the long chain alkyl carbon has from 12 to 16 carbon atoms. An especially practical quaternary ammonium saccharinate formulation is a commercially available product which is represented by a long chain substituted dimethyl-benzyl ammonium saccharinate, the product being a mixture of compounds where the long chain alkyl runs from $C_{12}$ to $C_{16}$. This is available commercially from Onyx Chemical Co. as ONYXIDE 3300.

Thus, the advent of the present invention affords an effective non-irritating deodorant composition with both bacteriocidal and bacteriostatic properties effective against odor development for prolonged periods of up to 24 hours or more. Furthermore, little or no skin irritation, sensitivity or abrasion is encountered even at high concentrations. Lastly, there is no adverse effect on clothing and the composition possesses a high shelf life stability.

The following examples are provided for illustrative purposes and they may include particular features of the invention. However, the examples should not be construed as limiting the invention, many variations of which are possible without departing from the spirit or scope thereof.

EXAMPLE I

A deodorant composition was prepared in cosmetic stick form by combining and warming the following ingredients, and then allowing the mixture to cool in a mold.

| | Parts |
|---|---|
| Alkyl dimethyl benzyl ammonium saccharinate[1] | 0.3 |
| Sodium Stearate | 8.0 |
| Propylene glycol | 15.0 |
| Ethanol | 65.0 |
| Water | 11.7 |
| Perfume | Trace |
| Colorant | Trace |

[1]ONYXIDE 3300, Onyx Chem. Co., mixture of dimethyl benzyl ammonium saccharinate alkyl (50% $C_{14}$; 40% $C_{12}$; 10% $C_{16}$)

EXAMPLE II

Evaluation of Deodorant Compositions By Zone of Inhibition Test

A composition similar to Example I in stick form but with no perfume or dye present was evaluated for antibacterial efficacy by the zone of inhibition method. A similar composition was also evaluated with the exception that a commercially available quaternary ammonium chloride composition at a 0.30 percent concentration was used in place of the saccharinate of Example I. (Quaternary chloride commercially available as Ethoquad 18/12 Surfactant.) A control with no antimicrobial compound was also run.

The test method may be described as follows:

Uniform discs "punched" from the stick containing the quaternary compound and with no fragrance or dye were placed on the surface of sterile, solidified agar. This was seeded with Staphylococcus epidermidis (A.T.C.C. No. 17917). This procedure was repeated with a similar stick containing no antimicrobial and no fragrance or dye as a control. The plates were incubated for 24 hours at 37°C. and then the zones read.

TABLE 1

| (Expressed as zone of bacterial inhibition) | |
|---|---|
| Product of Example I | 14 mm. zone |
| Similar product but with quaternary ammonium chloride derivative | 2 mm. zone — only a slight halo |
| Control | 0 mm. zone (no inhibition) |

Similar results are obtained using the saccharinate in the deodorant compositions at concentrations of 0.1; 0.5; and 1.0 percent by weight.

The results clearly demonstrate the efficacy of the saccharinate composition in contrast to the composition using a quaternary ammonium chloride known to have bactericidal action.

EXAMPLE III

Evaluation of Deodorant Compositions (Human Subjects)

Using the composition of Example I a panel of five male subjects applied the cosmetic deodorant conventionally to the axilla area.

All five subjects reported complete protection against odor development for 20 to 24 hours and no skin irritation. One subject also reported that no skin irritation was experienced with the test formulation whereas a similar formulation which differed only in that it contained well-known phenolic bactericide in place of the quaternary ammonium saccharinate, caused a definite skin irritation.

EXAMPLE IV

A deodorant composition was prepared in cosmetic stick form by combining and warming the following ingredients, and then allowing the mixture to cool in a mold.

| | Parts |
|---|---|
| Alkyl dimethyl benzyl ammonium saccharinate[1] | 0.3 |
| Sodium stearate | 8.0 |
| Propylene glycol | 66.7 |
| Glycerine | 5.0 |
| Water | 20.0 |

[1]ONYXIDE 3300, Onyx Chem. Co., mixture of alkyl dimethyl benzyl ammonium saccharinate (50% $C_{14}$; 40% $C_{12}$; 10% $C_{16}$)

We claim:

1. An improved deodorant composition comprising from about 5 to 10 percent by weight of an anionic base material which is an alkali metal salt of a long chain alkanoic acid of from 16 to 22 carbon atoms, from about 80 to 90 percent by weight of a lower alkanol and from 0.05 to 1 percent by weight of a quaternary ammonium saccharinate salt represented by the following formula:

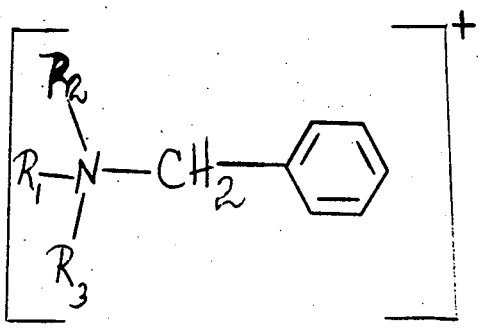 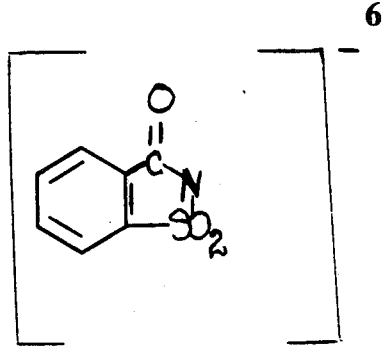

wherein $R_1$ is alkyl having from 8 to 16 carbon atoms and $R_2$ and $R_3$ are either methyl or ethyl; all percentages based on the weight of the total composition.

2. The composition according to claim 1 wherein the concentration of quaternary ammonium saccharinate is 0.25 percent.

3. The composition according to claim 1 wherein the base material is sodium stearate.

4. The composition according to claim 1 wherein the concentration is 7.5 percent.

5. The composition according to claim 1 wherein the lower alkanol is ethanol.

6. The composition according to claim 1 in gel stick form.

7. The composition according to claim 1 in which $R_1$ consists of a mixture of alkyls of 12, 14 and 16 carbon atoms.

8. The composition according to claim 1 comprising from about 5 to 15 weight percent glycerin.

9. The composition according to claim 8 wherein the lower alkanol is completely replaced by glycerin.

10. The composition according to claim 1 comprising from about 5 to 10 weight percent a propylene glycol.

11. The composition according to claim 10 wherein the lower alkanol is completely replaced by said propylene glycol.

* * * * *